(12) United States Patent
Droessler et al.

(10) Patent No.: US 6,657,197 B2
(45) Date of Patent: Dec. 2, 2003

(54) SMALL PROFILE SPECTROMETER

(75) Inventors: Justin G. Droessler, New Brighton, MN (US); Andrzej Peczalski, Eden Prairie, MN (US)

(73) Assignee: Honeywell International Inc., Morristowon, NJ (US)

( * ) Notice: Subject to any disclaimer, the term of this patent is extended or adjusted under 35 U.S.C. 154(b) by 75 days.

(21) Appl. No.: 09/747,032

(22) Filed: Dec. 22, 2000

(65) Prior Publication Data

US 2002/0079451 A1 Jun. 27, 2002

(51) Int. Cl.⁷ .............................................. G01N 21/35
(52) U.S. Cl. ............................. 250/339.12; 250/339.02
(58) Field of Search .......................... 250/339.11, 343, 250/339.13, 339.12, 339.02, 345; 356/445

(56) References Cited

U.S. PATENT DOCUMENTS

| | | | |
|---|---|---|---|
| 5,166,747 A | * 11/1992 | Schroeder et al. | 356/326 |
| 5,450,053 A | 9/1995 | Wood et al. | 338/18 |
| 5,600,148 A | 2/1997 | Cole et al. | 250/495.1 |
| 5,747,808 A | * 5/1998 | Wong | 250/343 |
| 5,895,233 A | 4/1999 | Higashi et al. | 438/107 |
| 6,037,591 A | * 3/2000 | Neri et al. | 250/339.11 |
| 6,119,031 A | * 9/2000 | Crowley | 600/407 |
| 6,128,075 A | * 10/2000 | Brierley | 356/244 |

* cited by examiner

*Primary Examiner*—Constantine Hannaher
*Assistant Examiner*—Timothy Moran
(74) *Attorney, Agent, or Firm*—Kris T. Fredrick

(57) ABSTRACT

A low profile spectrometer includes one or more electromagnetic energy emitters, one or more electromagnetic energy detectors, and an optical path including a sampling element. The optical path optically couples each of the one or more electromagnetic energy emitters to one of the one or more electromagnetic energy detectors. The one or more electromagnetic energy detectors and the one or more electromagnetic energy emitters are formed on a common substrate. The spectrometer may also include one or more first re-imaging elements for optically coupling the one or more electromagnetic energy emitters to the sampling element, and one or more second re-imaging elements for optically coupling the one or more electromagnetic energy detectors to the sampling element. The sampling element is capable of being optically coupled to a sample and provides a path for optically coupling the one or more first re-imaging elements to the one or more second re-imaging elements.

34 Claims, 4 Drawing Sheets

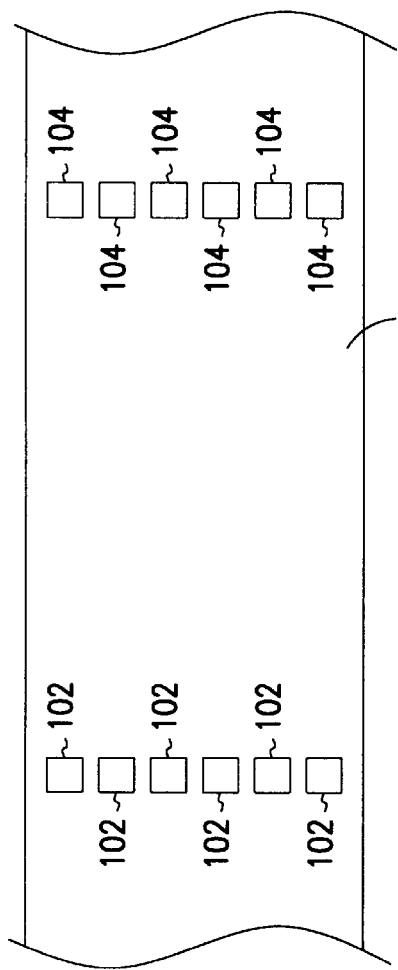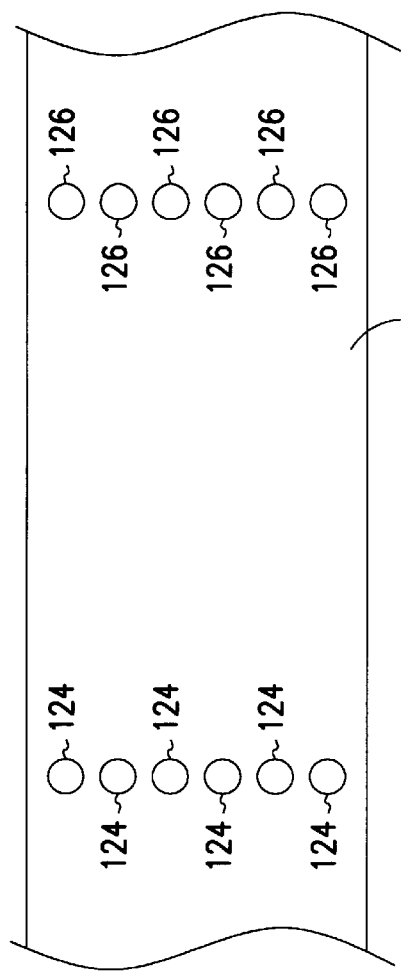

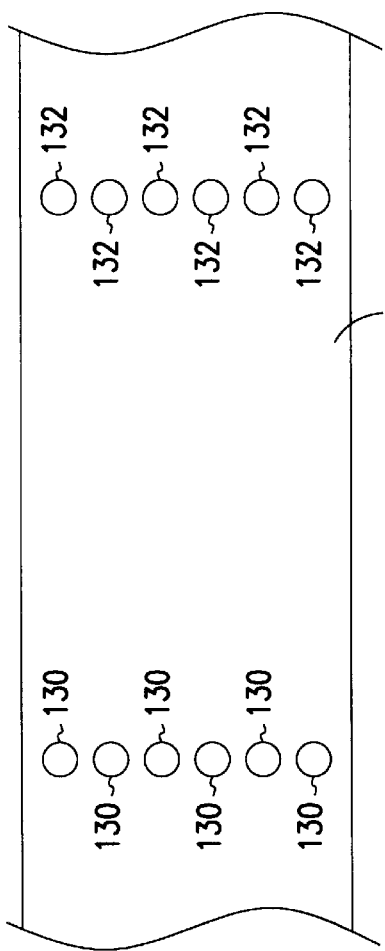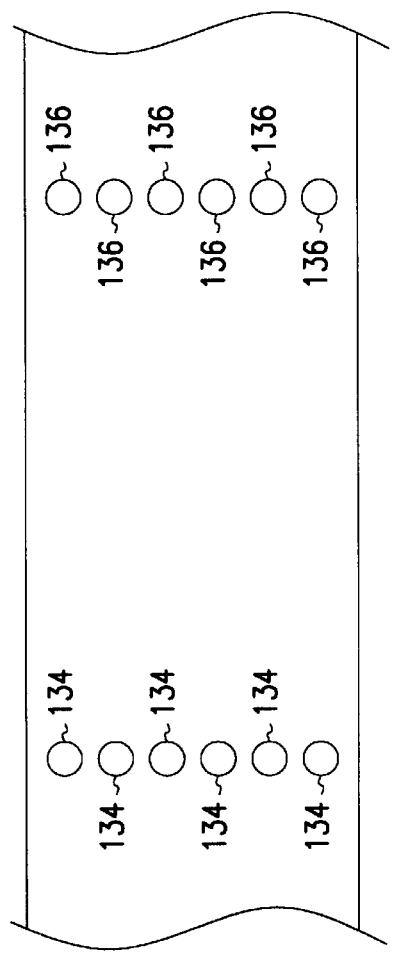

SMALL PROFILE SPECTROMETER

FIELD OF THE INVENTION

This invention relates to spectrometers, and more particularly, to small profile spectrometers.

BACKGROUND OF THE INVENTION

A spectrometer is an instrument for measuring the wavelengths of electromagnetic radiation. Typical laboratory spectrometers are bench size instruments and include a sample holder, a light source, an optical prism, and an electronics package. In operation, the light source illuminates a sample held by the sample holder, the optical prism separates light passing through the sample into wavelength bands, and the electronics package measures the intensity of the light in each of the wavelength bands. Spectrometers are often included in analytical instruments that identify the wavelengths of light absorbed by liquids, solids, and gases. Identifying absorbed wavelengths permits the identification of chemicals included in the liquids, solids, or gases being analyzed.

One application of laboratory spectrometers is the analysis of lubricants used in industrial machinery, such as earth moving equipment, aircraft, such as commercial jetliners, and long-haul trucks. By analyzing a lubricant, and identifying an optimum time for changing a lubricant in industrial machinery, aircraft, or long-haul trucks, the costs of operating such equipment can be reduced.

Lubricants are liquids or solids that reduce friction and wear of machine components, such as gears, in industrial, automotive, and transportation equipment. A machine component that requires lubrication will continue to perform satisfactorily as long as the lubricating oil or grease protecting it is kept clean and free from contaminants and abrasive particles, and the machine component itself does not deteriorate from wear. Lubricants can oxidatively break down, leading to the formation of degradation products. If oxidation becomes severe, the lubricant will corrode the critical surfaces of a component.

Monitoring lubricant quality during the course of machine operation is thus necessary to ensure optimal machine performance. Changes in lubricant properties such as viscosity or color may indicate that a lubricant has exceeded its useful life and must be changed. Changes in other properties, such as increases in the concentration of particulate matter, or changes in the level of chemical contaminants, may provide additional information about the wear of machine components. Lubricant monitoring typically requires interruption of machine operation to permit lubricant sampling. Samples are analyzed, typically offsite, by "wet bench" chemical techniques. These techniques can be costly and time-consuming. In addition, they are not performed in real time.

Infrared spectroscopy analysis using a laboratory spectrometer represents an alternative to "wet bench" methods. Fourier transform infrared spectroscopy, coupled with multivariate data analysis techniques, enhances the utility and sensitivity of infrared spectroscopy as a tool for lubricant quality analysis. The information contained in the infrared spectrum of a lubricant includes information at the molecular level about the chemical composition of the lubricant, the additives present, and the degradation products that were generated as a result of breakdown of the lubricant. Fourier transform infrared spectroscopy of lubricants can indicate whether and to what extent the lubricants have undergone oxidative degradation, as well as contamination due to free water, antifreeze, nitrogen fixation, soot deposits, and fuel dilution.

Unfortunately, infrared spectroscopy using laboratory spectrometers has several disadvantages. First, laboratory spectrometers are expensive. It is not uncommon to for a laboratory spectrometer to cost more than $15,000. Second, laboratory spectrometers are bulky and often occupy a space equivalent to the space taken up by a large desk. Third, a trained technician is often required to operate a laboratory spectrometer, which increases the cost of analyzing a sample. Fourth, samples for analysis must be brought to the laboratory spectrometer site for analysis.

For these and other reasons there is a need for the present invention.

SUMMARY OF THE INVENTION

The present invention provides a small profile spectrometer that can be used, in one embodiment, to monitor lubricant quality in machines. The spectrometer measures the absorption of electromagnetic energy in a lubricant at a specified frequency (or frequencies) characteristic of lubricants, lubricant breakdown products, or other contaminants.

In one embodiment a spectrometer is provided that includes one or more electromagnetic energy emitters, one or more electromagnetic energy detectors, and an optical path including a sampling element. The optical path optically couples each of the one or more electromagnetic energy emitters to one of the one or more electromagnetic energy detectors.

In an another embodiment, a method is provided that includes generating one or more infrared radiation beams, each of the one or more infrared radiation beams having an intensity, transmitting each of the one or more infrared radiation beams along an optical path that includes a sampling element optically coupled to a sample material to produce one or more attenuated infrared radiation beams, measuring the intensity of each of the one or more attenuated infrared radiation beams to produce one or more intensity measurements, and processing the one or more intensity measurements to identify one or more properties of the sample material.

BRIEF DESCRIPTION OF THE DRAWINGS

FIG. 1B is a top view of one embodiment of a substrate illustrating an arrangement of electromagnetic emitters and electromagnetic detectors according to the teachings of the present invention;

FIG. 1C is a top view of one embodiment of a substrate illustrating an arrangement of first re-imaging elements and second re-imaging elements according to the teachings of the present invention;

FIG. 1D is a top view of one embodiment of a substrate illustrating an arrangement of first aperture stops and second aperture stops according to the teachings of the present invention; and FIG. 1E is a top view of one embodiment of a substrate illustrating an arrangement of third re-imaging elements and third aperture stops.

DETAILED DESCRIPTION OF THE PREFERRED EMBODIMENTS

Figure 1A:
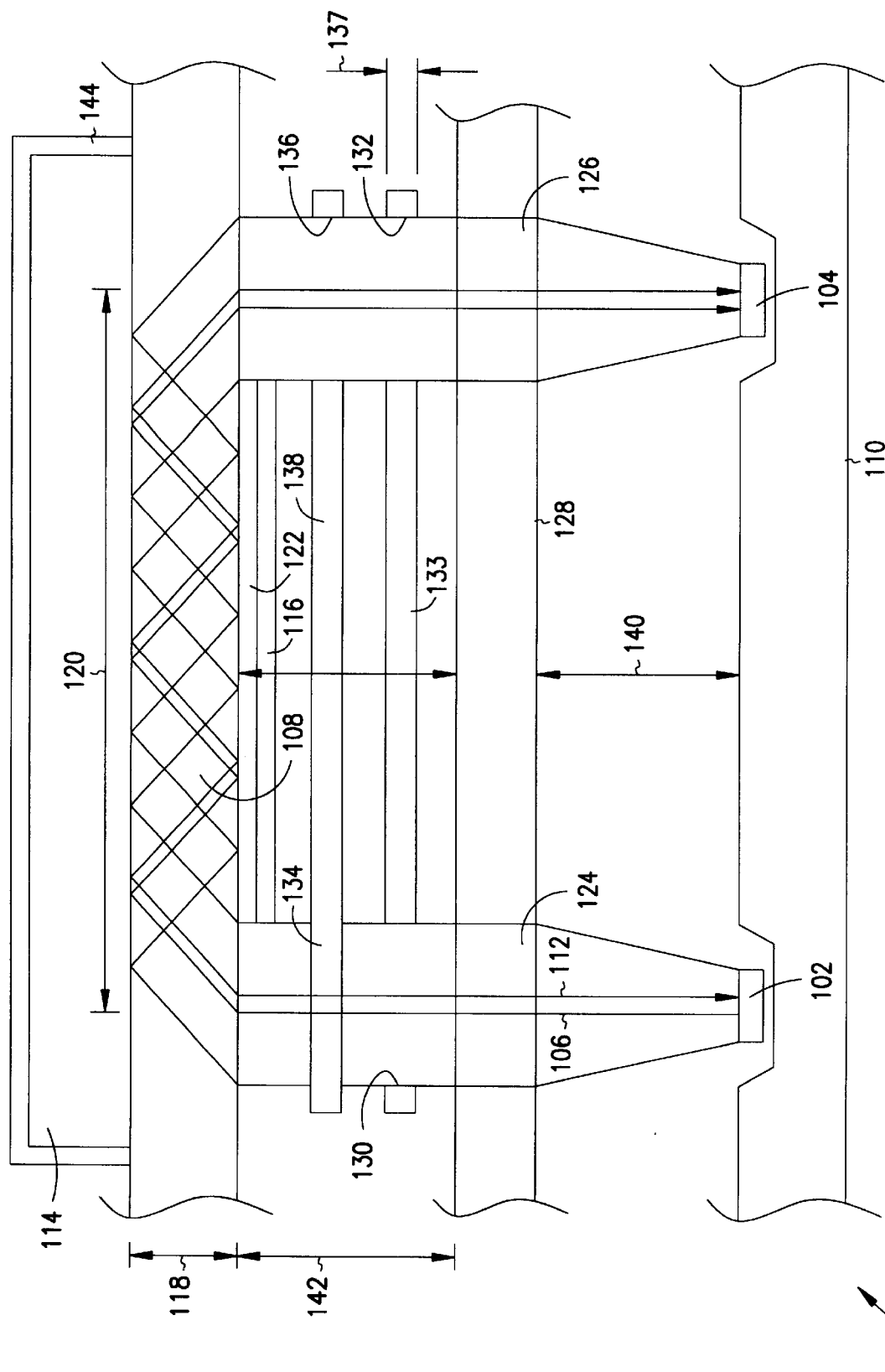
FIG. 1A is a cut-away optical path side view of some embodiments of a spectrometer according to the teachings of the present invention.

In the following detailed description of the invention, reference is made to the accompanying drawings which form a part hereof, and in which are shown, by way of illustration, specific embodiments of the invention which may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is not to be taken in a limiting sense, and the scope of the present invention is defined only by the appended claims, along with the full scope of equivalents to which such claims are entitled.

The present invention provides a spectrometer that permits continuous on-line, real-time lubricant analysis during machine operation. The spectrometer includes electromagnetic energy emitters, electromagnetic energy detectors, and a sampling element.

FIG. 1A is a cut-away optical path side view of some embodiments of a spectrometer 100 according to the teachings of the present invention. The spectrometer 100 includes one or more electromagnetic energy emitters 102, one or more electromagnetic energy detectors 104, and an optical path 106 including a sampling element 108. In one embodiment, each of the one or more electromagnetic energy emitters 102 and each of the one or more electromagnetic energy detectors 104 are fabricated on a substrate 110. The cost of fabricating the one or more electromagnetic energy emitters 102 and the one or more electromagnetic energy detectors 104 on a single substrate, such as substrate 110, is generally less than the cost of fabricating the one or more electromagnetic energy emitters 102 and the one or more electromagnetic energy detectors 104 on separate substrates.

The one or more electromagnetic energy emitters 102 are not limited to a particular type of emitter. In one embodiment, each of the one or more electromagnetic energy emitters 102 is a microbolometer emitter. The fabrication of microbolometers emitters is known in the art. When intended for operation in the infrared region of the electromagnetic spectrum, the microbolometer emitters 102 are operated at about 700 degrees Centigrade.

The one or more electromagnetic emitters 102 are not limited to operating at a particular electromagnetic frequency. In one embodiment, the electromagnetic energy emitters 102 operate in the infrared region of the electromagnetic spectrum. Preferably, when operating in the infrared region, the electromagnetic energy emitters 102 emit radiation having a wavelength of between about 2.5 micrometers and about 16.7 micrometers.

The one or more electromagnetic emitters 102 are not limited to being arranged in a particular geometrical pattern on the substrate 110 or to a particular number. FIG. 1B shows a top view of one embodiment of the substrate 110 illustrating a linear arrangement of six electromagnetic emitters 102 suitable for use in connection with the spectrometer 100 according to the teachings of the present invention. In another embodiment, the number of one or more electromagnetic emitters 102 is between about twenty and about thirty. For a linear arrangement of between about twenty and about thirty electromagnetic emitters 102, the infrared spectrum with wavelengths between about 2.5 micrometers and about 16.7 micrometers is divided into wavelength bands of between about 0.5 micrometers and about 0.7 micrometers for processing.

The one or more electromagnetic energy detectors 104 are not limited to a particular type of detector. In one embodiment, each of the one or more electromagnetic energy detectors 104 is a microbolometer detector. The fabrication of microbolometer detectors is known in the art. In operation, a microbolometer detector changes resistance in response to electromagnetic radiation. In one embodiment, the change in resistance is detected by providing a constant current to the microbolometer detector and measuring a change in voltage across the microbolometer detector.

The number of electromagnetic energy detectors 104 is selected to be equal to the number of electromagnetic energy emitters 102. The one or more electromagnetic detectors 104 are not limited to being arranged in a particular geometrical pattern on the substrate 110 or to a particular number.

FIG. 1B is a top view of one embodiment of the substrate 110 illustrating an arrangement of six electromagnetic energy emitters 102 and an arrangement of six electromagnetic energy detectors 104. As can be seen in FIG. 1B, the six electromagnetic energy emitters 102 are arranged linearly, and the six electromagnetic energy detectors 104 are arranged linearly.

Referring again to FIG. 1A, in another embodiment, the number of electromagnetic energy detectors is between about twenty and about thirty. In operation, each of the one or more electromagnetic energy detectors 104 receives energy from one of the one or more electromagnetic energy emitters 102.

The fabrication and packaging of electromagnetic emitters 102 and electromagnetic detectors 104 is described in the following United States patents: U.S. Pat. Nos. 5,600,148, 6,046,485, and 5,895,233, which are incorporated herein by reference.

The optical path 106 optically couples each of the one or more electromagnetic energy emitters 102 to one of the one or more electromagnetic energy detectors 104. The optical path 106 includes the path that electromagnetic radiation emitted by any of the one or more electromagnetic energy emitters 102 travels to arrive at an associated electromagnetic detector. The optical path 106 has an optical path length 112 defined as the shortest optical distance between one of the one or more electromagnetic energy emitters 102 and one of the one or more electromagnetic energy detectors 104. In one embodiment, the optical path length 112 is between about one millimeter and about fifteen millimeters.

The sampling element 108 is included in the optical path 106. In one embodiment, the sampling element 108 is a crystal. Materials suitable for use in forming the sampling element 108 include but are not limited to KRS5, silicon, diamond, zinc, selenide, and zinc selenide. The particular material selected for use in forming the sampling element 108 may be selected to provide a particular level of transparency or to provide a particular degree of optical coupling to a sample 114. In one embodiment, the sampling element 108 is fabricated as a separate stand-alone element. In another embodiment, the sampling element 108 is formed on a substrate 116. Forming the sampling element 108 on the substrate 116 permits the fabrication of a thin sampling element. In one embodiment, the sampling element 108 has a thickness 118 of between about five microns and about fifteen microns. One method of forming the sampling element 108 on the substrate 116 is to deposit a sampling element material, such as KRS5, silicon, diamond, zinc, selenide, or zinc selenide, on a surface of the substrate 116 by chemical vapor deposition. Materials suitable for use as the substrate 116 are preferably transparent to infrared energy. Exemplary materials suitable for use in fabricating the substrate 116 include but are not limited to silicon and germanium.

The sampling element 108 has a sampling element length 120. The sampling element length 120 is selected to provide detectable attenuation by the sample 114 of the electromagnetic energy emitted by the one or more electromagnetic emitters 102. The amount of attenuation of the electromagnetic energy passing through the sampling element 108 is also influenced by the number of reflections of the electromagnetic energy in the sampling element 108. In one embodiment, the sampling element length 120 is between about five millimeters and about ten millimeters. In another embodiment, the sampling element length 120 is selected to allow between about one and about 150 reflections as the electromagnetic radiation passes through the sampling element 108. In one embodiment, the sampling element 108 transmits electromagnetic energy by total internal reflection. In another embodiment, the sampling element 108 transmits electromagnetic energy by having at least one mirrored surface 122. Mirroring one surface of the sampling element 108 decreases the need for total internal reflection in the sampling element 108. In one embodiment, a surface of the sampling element 108 is coated with a material that reflects infrared radiation. Materials suitable for coating a surface of the sampling element 108 to form an infrared reflecting surface include aluminum, silver, and gold. Chemical vapor deposition is one coating process suitable for use in applying aluminum, silver, or gold to one surface of the sampling element 108.

The optical path 106 may include optical elements in addition to the sampling element 108. In one embodiment, the optical path 106 includes one or more first re-imaging elements 124 for optically coupling the one or more electromagnetic energy emitters 102 to an input port of the sampling element 108 and the one or more second re-imaging elements 126 for optically coupling an output port of the sampling element 108 to the one or more electromagnetic energy detectors 104. Each of the one or more first re-imaging elements 124 converts diffuse electromagnetic energy from each of the one or more electromagnetic energy emitters 102 into an optical beam for transmission to an input port of the sampling element 108. Each of the one or more first re-imaging elements 124 is preferably designed to transmit a band of electromagnetic energy. In this way the attenuation of discrete energy bands can be measured after the electromagnetic energy passes through the sampling element 108 and is detected at the one or more electromagnetic detectors 104. The first re-imaging elements 124 are not limited to a particular type of re-imaging element. In one embodiment, each of the first re-imaging elements 124 is a collimating lens which converts the diffuse energy from one of the one or more electromagnetic energy emitters 102 into a non-diffuse optical beam. In another embodiment, each of the first re-imaging elements 124 is a diffractive lens which converts the diffuse energy from one of the one or more electromagnetic energy emitters 102 into a non-diffuse optical beam.

For the spectral analysis of lubricants, infrared radiation in the range of 2.5 $\mu$m to 16.7 $\mu$m is filtered into 23 bands, each of the 23 bands being between about 0.2 microns and about 0.4 microns wide. The one or more first re-imaging elements 124 number 23, one for each small waveband, designed with different focal lengths, such that there is only one common back focal distance for all 23 small wavebands.

Each of the one or more second re-imaging elements 126 converts an optical beam from an output port of the sampling element 108 into a focused optical beam for detection at the one or more electromagnetic energy detectors 104. A focused optical beam concentrates the energy in the optical beam to a small area occupied by one of the one or more electromagnetic energy detectors 104. In the preferred embodiment, the one or more first re-imaging elements 124 and the one or more second re-imaging elements 126 are formed on a common substrate 128. Forming the one or more first re-imaging elements 124 and the one or more second re-imaging elements 126 on the common substrate 128 simplifies the process for aligning the one or more electromagnetic radiation emitters 102 with the first re-imaging elements 124 and aligning the one or more electromagnetic radiation detectors 104 with the second re-imaging elements 126. The alignment process is simplified because only the substrate 110 and the common substrate 128 need to be aligned in order to align the electromagnetic energy emitters 102 with the one or more first re-imaging elements 124 and the electromagnetic energy detectors 104 with the one or more second re-imaging elements 126.

FIG. 1C is a top view of one embodiment of the substrate 128 illustrating an arrangement of six first re-imaging elements 124 and an arrangement of six second re-imaging elements 126. As can be seen in FIG. 1C, the six first re-imaging elements 124 are arranged linearly, and the six second re-imaging elements 126 are arranged linearly.

Referring again to FIG. 1A, in another embodiment, in addition to the one or more first re-imaging elements 124 and the one or more second re-imaging elements 126, the optical path 108 includes one or more first aperture stops 130 and one or more second aperture stops 132. The one or more first aperture stops 130 are located between the first re-imaging elements 124 and the input port of the sampling element 108. The one or more first aperture stops 130 assist in waveband selection for the output of the one or more electromagnetic energy emitters 102 at the input port of the sampling element 108. The one or more second aperture stops 132 are located between the output port of the sampling element 108 and the one or more second re-imaging elements 126. The one or more second aperture stops 132 assist in imaging and focusing the radiation at the output port of the sampling element 108 onto the one or more electromagnetic detectors 104.

FIG. 1D is a top view of one embodiment of the substrate 133 illustrating an arrangement of six first aperture stops 130 and an arrangement of six second aperture stops 132. As can be seen in FIG. 1D, the six first aperture stops 130 are arranged linearly, and the six second aperture stops 132 are arranged linearly.

Referring again to FIG. 1A, in yet another embodiment, in addition to the re-imaging elements and apertures described above, the optical path 106 includes one or more third re-imaging elements 134 and the one or more third aperture stops 136. The one or more third re-imaging elements 134 are located between the one or more first aperture stops 130 and the input port of the sampling element 108. In one embodiment, each of the one or more third re-imaging elements 134 is a diffractive lens. The one or more third aperture stops 136 are located between the output port of the sampling element 108 and the one or more second aperture stops 132. The one or more third aperture stops 136 further assist in transmitting the optical beam produced at the output port of the sampling element 108 to the one or more electromagnetic energy detectors 104. The one or more third re-imaging elements 134 and the one or more third aperture stops 136 are preferably formed on a single substrate 138.

FIG. 1E is a top view of one embodiment of the substrate 138 illustrating an arrangement of six third re-imaging elements 134 and an arrangement of six third aperture stops 136. As can be seen in FIG. 1E, the six re-imaging elements 134 are arranged linearly, and the six third aperture stops 136 are arranged linearly.

Referring again to FIG. 1A, in another embodiment, the one or more first re-imaging elements 124 are substantially identical, and the substrate 133 has a thickness 137. The thickness 137 determines the spacing between the one or more first aperture stops 130 and the one or more first re-imaging elements 124. The spacing defines the breadth of the wavelength band transmitted by each of the one or more first aperture stops 130. Varying the thickness 137 of the substrate 133 to control the breadth of the transmitted wavelength band simplifies the fabrication of the one or more first re-imaging elements 124.

In assembling the spectrometer 100, the substrate 110 is located at a distance 140 from the substrate 128. In one embodiment, the distance 140 is between about 0.25 millimeters and about 0.75 millimeters. Thus each of the one or more first re-imaging elements 124 and each of the one or more second re-imaging elements 126, which are formed on the substrate 128, are located an equal distance from the substrate 110. The substrate 128 is preferably located at a distance 142 of between about 0.05 millimeters and about 1.5 millimeters from the sampling element 108. Designing each of the one or more first re-imaging elements 124 and each of the one or more second re-imaging elements 126 to permit locating the substrate 128 at a fixed distance from the sampling element 108 and a fixed distance from the substrate 110 simplifies the assembly of the spectrometer 100.

In the operation of one embodiment of the spectrometer 100, the optical path 106 includes one or more re-imaging lenses 124 to focus the infrared radiation emitted by the one or more electromagnetic radiation emitters 102 onto the one or more apertures 130. The one or more re-imaging lenses 124 disperses the infrared radiation longitudinally in wavelength along its optical axis. Each of the one or more apertures 130 selects a given waveband to be passed on to the one or more third re-imaging elements 134. (The size of the waveband is determined by the diameter of the aperture 130.) The one or more third re-imaging elements collimate the waveband of radiation passed by the one or more apertures 130 from one or more electromagnetic radiation emitters 102. Each of the one or more re-imaging elements 124 is preferably a diffractive lens that is capable of focusing a different range of wavelengths onto one of the one or more apertures 130.

A method of determining properties of the sample 114 using the spectrometer 100 of the present invention includes transmitting infrared radiation through the optical path 106 that includes an interface between the sampling element 108 and the sample 114, measuring the intensity of the infrared radiation after the radiation passes through the sampling element 108, and processing the intensity measurements to identify one or more properties of the sample material. The infrared radiation is coupled to the sampling element 108 at an angle such that the radiation travels through the sampling element 108 by total internal reflection. At the interface between the sample 114 and the sampling element 108 an evanescent wave is created that extends beyond the surface of the sampling element into the sample 114. The resulting absorbance is proportional to the number of reflections of the infrared beam in the sampling element 108 and the depth of penetration of the evanescent wave into the sample 114. In regions of the infrared spectrum where the sample 114 absorbs energy, the evanescent wave is attenuated. The altered (attenuated) energy from each evanescent wave is passed back to the sampling element 108. The electromagnetic energy exits the sampling element 108 at the output port of the sampling element and is directed to one of the one or more electromagnetic energy detectors 104.

In one embodiment, the spectrometer 100 is coupled to the reservoir 144 to analyze a sample 114 contained in the reservoir 144. The method of coupling is not limited to a particular method. Any method that permits optical coupling of the sampling element 108 to the sample 114 is suitable for use in connection with coupling the spectrometer 100 to the reservoir 144. One exemplary method of coupling the spectrometer 100 to the reservoir 144 comprises providing a threaded housing for the spectrometer 100, tapping a hole in the reservoir 144, and mating the threaded housing to the tapped hole in the reservoir 144.

Figure 2:
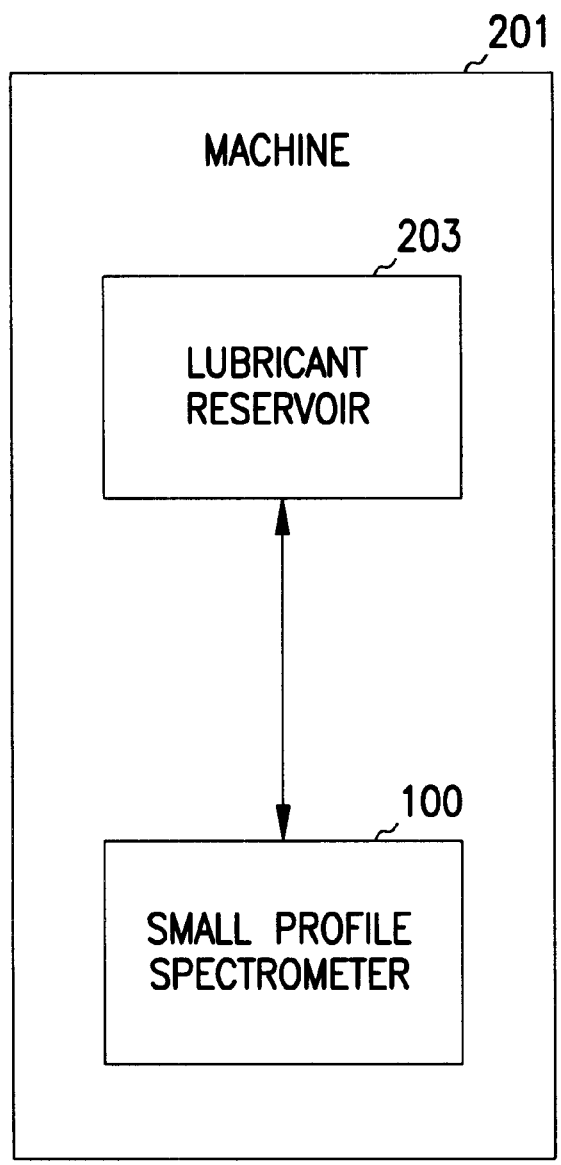
FIG. 2 is a block diagram of a machine including a lubricant reservoir optically coupled to a spectrometer according to the teachings of the present invention.

FIG. 2 is a block diagram of a machine 201 including a lubricant reservoir 203 optically coupled to the spectrometer 100 according to the teachings of the present invention. In one embodiment, the spectrometer 100 includes a package having dimensions of about 4×4×8 millimeters. In another embodiment, the spectrometer 100 has a length of between about 1.5 millimeters and about 4.5 millimeters, a width of between about 1.5 millimeters and about 4.5 millimeters, and a thickness of between about 2.5 millimeters and about 6.5 millimeters. The small package size permits the spectrometer 100 to be retrofitted into existing machinery or easily designed into new machinery. The machine 201 is not limited to a particular type of machine. Any machine that requires lubrication is suitable for use in connection with the present invention. The lubricant reservoir 203 contains the sample material, such as oil, grease, hydraulic fluid, or a combination thereof. Identifying one or more properties of the sample material includes a determination of the concentration of contaminants and degradation products in the sample material. Contaminants may be soot, water, oxidative degradation products, nitrated materials, glycol, sugar, gasoline, diesel fuel, sulfates, or the like. In one embodiment, the machine 201 is a truck. In another embodiment, the machine 201 is plane. In still another embodiment, the machine is ship. Those skilled in the art appreciate that the spectrometer 100 is readily interfaced to a computing system capable of analyzing signals returned from the one or more detectors 104, shown in FIG. 1A. Analytical results may be displayed on the operation console of a machine. For example, a "lubricant quality" warning button or switch on a machine console that is attached to the processor programmed to illuminate or sound an alarm if lubricant quality drops below a designated level. The microprocessor optionally may be programmed for an automatic machine "shut down" if the concentration of contaminants and degradation products in the lubricant sample reaches an unacceptable level.

Although specific embodiments have been described and illustrated herein, it will be appreciated by those skilled in the art, having the benefit of the present disclosure, that any arrangement which is intended to achieve the same purpose may be substituted for a specific embodiment shown. This application is intended to cover any adaptations or variations of the present invention. Therefore, it is intended that this invention be limited only by the claims and the equivalents thereof.

What is claimed is:

1. A spectrometer comprising:
one or more electromagnetic energy emitters;
one or more electromagnetic energy detectors; and
an optical path including a sampling element structured for being optically coupled to a non-gaseous sample, the optical path for optically coupling each of the one or more electromagnetic energy emitters to one of the one or more electromagnetic energy detectors, wherein each of the one or more electromagnetic energy emitters and each of the one or more electromagnetic energy detectors are formed on a common substrate.

2. A spectrometer comprising:
one or more electromagnetic energy emitters;
one or more electromagnetic energy detectors; and
an optical path including a sampling element structured for being optically coupled to a non-gaseous sample, the optical path for optically coupling each of the one or more electromagnetic energy emitters to one of the one or more electromagnetic energy detectors, wherein each of the one or more electromagnetic energy emitters and each of the one or more electromagnetic energy detectors are formed on a common substrate and each of the one or more electromagnetic energy emitters comprises a microbolometer emitter capable of emitting infrared energy.

3. A spectrometer comprising:
one or more electromagnetic energy emitters;
one or more electromagnetic energy detectors; and
an optical path including a sampling element structured for being optically coupled to a non-gaseous sample, the optical path for optically coupling each of the one or more electromagnetic energy emitters to one of the one or more electromagnetic energy detectors, wherein the one or more electromagnetic energy emitters comprise between about twenty and about thirty electromagnetic energy emitters and the one or more electromagnetic energy detectors comprise between about twenty and about thirty electromagnetic energy detectors formed on a substrate and the between about twenty and about thirty electromagnetic energy emitters are formed on the substrate.

4. A spectrometer comprising:
one or more electromagnetic energy emitters;
one or more electromagnetic energy detectors; and
an optical path including a sampling element structured for being optically coupled to a non-gaseous sample, the optical path for optically coupling each of the one or more electromagnetic energy emitters to one of the one or more electromagnetic energy detectors, wherein the optical path comprises:
one or more first re-imaging elements for optically coupling the one or more electromagnetic energy emitters to the sampling element; and
one or more second re-imaging elements for optically coupling the one or more electromagnetic energy detectors to the sampling element, wherein the sampling element provides a path for optically coupling the one or more first re-imaging elements to the one or more second re-imaging elements.

5. The spectrometer of claim 4, wherein the sampling element comprises a crystal.

6. The spectrometer of claim 5, wherein the crystal is fabricated on a substrate.

7. The spectrometer of claim 6, wherein the crystal has at least one mirrored surface.

8. The spectrometer of claim 4, wherein the sampling element comprises a material that is substantially transparent to infrared energy.

9. The spectrometer of claim 4, wherein each of the one or more first re-imaging elements comprises a diffractive lens.

10. The spectrometer of claim 4, wherein each of the one or more first re-imaging elements comprises a collimating lens.

11. The spectrometer of claim 4, wherein each of the one or more second re-imaging elements comprises a focusing lens.

12. The spectrometer of claim 4, wherein each of the one or more electromagnetic radiation sources is capable of generating infrared radiation having a wavelength of between about 2.5 micrometers and about 16.7 micrometers.

13. The spectrometer of claim 4, further comprising one or more aperture stops located in the optical path.

14. The spectrometer of claim 4, wherein each of the one or more first re-imaging elements and each of the one or more second re-imaging elements are located an equal distance from a substrate.

15. The spectrometer of claim 4, wherein each of the one or more first re-imaging elements and each of the one or more second re-imaging elements are located at a distance of between about 0.05 to 1.5 millimeters from the sampling element.

16. The spectrometer of claim 4, further comprising:
a reservoir containing a lubricant, the lubricant being optically coupled to the sampling element.

17. A spectrometer comprising:
a first substrate comprising one or more infrared radiation emitters and one or more infrared radiation detectors formed thereon;
a second substrate comprising a plurality of re-imaging elements formed thereon;
a third substrate comprising a plurality of apertures formed thereon;
a fourth substrate comprising one or more re-imaging elements and one or more apertures formed thereon; and
a fifth substrate comprising a sampling element formed thereon, wherein the first substrate, the second substrate, the third substrate, and the fourth substrate are arranged such that an optical path coupling the one or more infrared radiation emitters to the one or more infrared radiation detectors is formed.

18. The spectrometer of claim 17, wherein the spectrometer has a length of between about 1.5 millimeters and about 4.5 millimeters, a width of between about 1.5 millimeters and about 4.5 millimeters, and a thickness of between about 2.5 millimeters and about 6.5 millimeters.

19. The spectrometer of claim 17, wherein the first substrate comprises silicon and the fifth substrate comprises germanium.

20. The spectrometer of claim 17, further comprising:
a reservoir containing a lubricant, the lubricant being optically coupled to the sampling element.

21. A method comprising:
generating a plurality of infrared radiation beams from a plurality of electromagnetic energy emitters, each of the plurality of infrared radiation beams having a different wavelength band;

transmitting each of the plurality of infrared radiation beams along an optical path that includes a sampling element optically coupled to a sample material to produce a plurality of attenuated infrared radiation beams;

measuring the intensity of each of the plurality of attenuated infrared radiation beams to produce a plurality of intensity measurements; and processing the plurality of intensity measurements to identify one or more properties of the sample material.

22. The method of claim 21, wherein generating a plurality of infrared radiation beams from a plurality of electromagnetic energy emitters comprises:

passing a current through a plurality of bolometer emitters to generate the plurality of infrared radiation beams; and separately collimating each of the plurality of infrared radiation beams such that each of the plurality of infrared radiation beams includes a substantially unique range of infrared wavelengths.

23. The method of claim 21, wherein processing the plurality of intensity measurements to identify one or more properties of the sample material comprises:

determining a concentration value for a contaminant in the sample material.

24. A method comprising:

generating a plurality of infrared radiation beams, each of the plurality of infrared radiation beams having a different wavelength band;

transmitting each of the plurality of infrared radiation beams along an optical path that includes a sampling element optically coupled to a sample material to produce a plurality of attenuated infrared radiation beams;

measuring the intensity of each of the plurality of attenuated infrared radiation beams to produce a plurality of intensity measurements;

processing the plurality of intensity measurements to identify one or more properties of the sample material;

wherein generating a plurality of infrared radiation beams comprises:

passing a current through one or more bolometer emitters to generate the one or more infrared radiation beams; and separately collimating each of the plurality of infrared radiation beams such that each of the plurality of infrared radiation beams includes a substantially unique range of infrared wavelengths; and wherein separately collimating each of the plurality of infrared radiation beams such that each of the plurality of infrared radiation beams includes a substantially unique range of infrared wavelengths comprises:

placing one or more collimating lenses having different dispersing factors in each of the plurality of infrared radiation beams.

25. A spectrometer comprising:

one or more electromagnetic energy emitters;

one or more electromagnetic energy detectors; and an optical path including a sampling element, the optical path for optically coupling each of the one or more electromagnetic energy emitters to one of the one or more electromagnetic energy detectors;

one or more first re-imaging elements for optically coupling the one or more electromagnetic energy emitters to the sampling element;

one or more second re-imaging elements for optically coupling the one or more electromagnetic energy detectors to the sampling element, wherein the sampling element provides a path for optically coupling the one or more first re-imaging elements to the one or more second re-imaging elements; and wherein the sampling element comprises a crystal.

26. A spectrometer comprising:

an electromagnetic energy emitter;

an electromagnetic energy detector; and an optical path coupling the electromagnetic energy emitter to the electromagnetic energy detector, the optical path including a sampling element that at least partially comprises a crystal formed on a substrate, the sampling element being structured to be optically coupled to a non-gaseous sample.

27. The spectrometer of claim 26 wherein the sampling element has a thickness between about five microns and about fifteen microns.

28. The spectrometer of claim 26 wherein the crystal is zinc selenide.

29. The spectrometer of claim 26 wherein the crystal is formed on the substrate by chemical vapor deposition.

30. The spectrometer of claim 26 wherein the substrate is transparent to infrared energy.

31. The spectrometer of claim 26 wherein the substrate is silicon.

32. The spectrometer of claim 26 wherein a surface of the sampling element is coated with a material that reflects infrared energy.

33. The spectrometer of claim 32 wherein the material is coated on the sampling element by chemical vapor deposition.

34. The spectrometer of claim 32 wherein the material is aluminum.

* * * * *